United States Patent [19]

Conrow

[11] Patent Number: 6,040,468

[45] Date of Patent: Mar. 21, 2000

[54] METHOD OF PREPARING 16α, 17α-DIALKYLATED STEROIDS

[75] Inventor: Raymond E. Conrow, Crowley, Tex.

[73] Assignee: Alcon Laboratories, Inc., Fort Worth, Tex.

[21] Appl. No.: 09/186,975

[22] Filed: Nov. 5, 1998

Related U.S. Application Data

[60] Provisional application No. 60/067,148, Dec. 2, 1997.

[51] Int. Cl.$^7$ ................................. C07J 9/00; C07J 5/00; C07J 7/00; C07J 71/00
[52] U.S. Cl. ......................... 552/543; 552/543; 552/552; 552/544; 552/546; 552/553; 552/540; 552/557; 552/599; 552/601; 540/87
[58] Field of Search ..................... 552/540, 543, 552/544, 546, 505, 552, 559, 557; 540/87

[56] References Cited

U.S. PATENT DOCUMENTS

| | | | |
|---|---|---|---|
| 3,862,194 | 1/1975 | Woods et al. | 260/397.3 |
| 3,947,478 | 3/1976 | Woods et al. | 260/397.3 |
| 4,686,214 | 8/1987 | Boltralik | 514/179 |
| 4,704,455 | 11/1987 | VanRheenen et al. | 540/87 |
| 4,891,426 | 1/1990 | VanRheenen et al. | 540/4 |
| 4,929,395 | 5/1990 | VanRheenen et al. | 540/4 |
| 4,990,612 | 2/1991 | VanRheenen et al. | 540/89 |

FOREIGN PATENT DOCUMENTS

| | | |
|---|---|---|
| 0 263 213 A1 | 10/1986 | European Pat. Off. . |
| 0 574 318 A1 | 12/1993 | European Pat. Off. . |
| 0 608 178 A1 | 7/1994 | European Pat. Off. . |

OTHER PUBLICATIONS

Boncza–Tomaszewski et al., "Steroids and related products. L. The synthesis of 17–methoxymethylprogesterone," *Steroids*, vol. 39(1), pp. 107–114 (1982).

Binkley, et al., "Regiospecific Alkylation of Enolate Ions in Liquid Ammonia–Tetrahydrofuran," *J. Org. Chem.*, vol. 40, p. 2156 (1975).

Cairns, et al., "Alkylated Steroids. Part 3.1 The 21–Alkylation of 20–Oxopregnanes and Synthesis of a Novel Anti–inflammatory 16α, 17α21–Trimethyl Steroid (Org 6216)," *J. Chem. Soc., Perkin Trans. I*, p. 2306 (1981).

Cairns, et al., "Alkylated Steroids. Part 1. 16α–Substituted 17α–Methylpregnanes," *J. Chem. Soc., Perkin Trans. I*, p. 1558 (1976).

Cairns, et al., "Alkylated Steroids. Part 2.$^1$ 16α,17α–Dimethylpregnanes functionalised in Ring," *J. Chem. Soc., Perkin Trans. I*, p. 1594 (1978).

Gooding et al., "Triply Convergent Synthesis of 15–(Phenoxymethyl) and 4,5–Allenyl Prostaglandins. Preparation of an Individual Isomer of Enprostil," *J. Org. Chem.*, vol. 58, p. 3681 (1993).

Horiguchi et al., "Double Hydroxylation Reaction for Construction of the Corticoid Side Chain: 16α–Methylcortexolone," *Org. Synth.*, vol. 73, p. 123 (1995).

Kuwajima, et al., "Fluoride–Mediated Reactions of Enol Silyl Ethers. Regiospecific Monoalkylation of Ketones," *J. Am. Chem. Soc.*, vol. 104, p. 1025 (1982).

Patterson, et al., "Synthesis of Prostaglandins by Conjugate Addition and Alkylation of a Directed Enolate Ion. 11–Deoxyprostaglandins," *J. Org. Chem.*, vol. 39, p. 2506 (1974).

Schaub, et al., "The Synthesis of Certain 17α–Alkyl Corticoids," *J. Med Chem.*, vol. 10, p. 789 (1967).

VanRheenen et al., "16α–Methyl steroids," *Chemical Abstracts*, vol. 105, p. 675 (1986).

VanRheenen et al., "Process for the 16α–methylation of 16–unsaturated corticoids," *Chemical Abstracts*, vol. 108, p. 674 (1988).

*Primary Examiner*—Jose' G. Dees
*Assistant Examiner*—Sabiha N. Qazi
*Attorney, Agent, or Firm*—Patrick M. Ryan

[57] ABSTRACT

16α, 17α-dialkylated steroids are prepared by reacting a 16α-alkyl-17(20)-enyl-20-silyl ether with an alkylating agent and an enol silyl ether cleaving agent in a suitable solvent.

9 Claims, No Drawings

METHOD OF PREPARING 16α, 17α-DIALKYLATED STEROIDS

This application claims priority from co-pending U.S. Provisional Patent Application Ser. No. 60/067,148 filed Dec. 2, 1997.

FIELD OF THE INVENTION

The present invention relates to methods of synthesizing 16α, 17α-dialkylated steroids. In particular, the present invention relates to methods of appending a 17α-alkyl substituent to a steroidal 16α-alkyl-17(20)-enyl-20-silyl ether.

BACKGROUND OF THE INVENTION

16α, 17α-dialkylated steroids have desirable medicinal properties. See, for example, U.S. Pat. No. 4,686,214; Cairns, et al., J. Chem. Soc., Perkin Trans. I, 1981:2306, and references cited therein.

Previous syntheses of 16α, 17α-dialkylated steroids have employed a one-step conjugate addition-enolate trapping method to accomplish the addition of the C16 and C17 alkyl groups. For example, see Schaub, et al., J. Med. Chem., 10:789 (1967), and Cairns, et al., J. Chem. Soc., Perkin Trans. I, 1978:1594 and 1976:1558, disclosing alkyl Grignard conjugate addition reaction followed by an alkyl halide quench in a single reaction vessel.

The one-step conjugate addition-enolate trapping method sometimes gives the desired 16α, 17α-dialkylated steroid in low yield and contaminated with polyalkylated side products. Such side products can be difficult to remove using conventional purification techniques, e.g., recrystallization: Cairns, et al., J. Chem. Soc., Perkin Trans. I, 1981:2306 and 1978:1594.

Alternative methods of preparing 16α, 17α-dialkylated steroids are desired.

SUMMARY OF THE INVENTION

According to the present invention, steroidal 16α-alkyl-17(20)-enyl-20-silyl ethers are reacted with an enol silyl ether cleaving agent and an alkylating agent to give the corresponding 16α, 17α-dialkylated steroid.

DETAILED DESCRIPTION OF THE INVENTION

Enones of Formula I are known. The compounds of Formula I can be prepared, for example, according to the methods cited or disclosed in commonly assigned, co-pending Patent Application No. PCT/US97/19276, titled "METHOD OF PREPARING 21-ALKYLATED PREGNA-1,4,16-TRIEN-3,20-DIONES," filed Oct. 22, 1997, which claims priority from parent U.S. provisional application Ser. No. 60/029,312, filed Oct. 25, 1996.

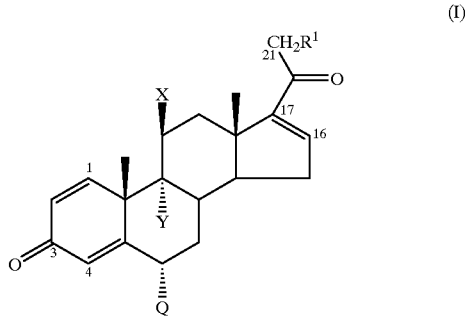

wherein $R^1$ is H or $CHR^4R^5$;
X is $OSiR^7R^8R^9$ or $OC(=O)R^6$;
Y is H, F, or Cl; or X and Y taken together are a covalent bond;
or
X and Y taken together form an epoxide group:

$R^4$, $R^5$ and $R^6$ are independently H or $C_1$–$C_4$ alkyl;
$R^7$, $R^8$ and $R^9$ are independently $C_1$–$C_4$ alkyl; and
Q is H or $CH_3$.

Enol silyl ethers of Formula II can be prepared by addition of a stoichiometric organocuprate reagent and a silylating agent to enones of Formula I, as described in Example 1 below. Alternatively, a catalytic organocuprate reagent can be used, as described by Horiguchi et al., Org. Synth., 73:123 (1995) for the case of copper-catalyzed Grignard addition to 16-dehydroprogesterone. Generally, it is desirable to conduct this addition reaction at low temperatures to increase the yield of the intended alkylation product. Appropriate temperatures will be determined by those skilled in the art, but will typically range from 0 to −100° C. In most instances, it is expected that temperatures ranging from −20 to −80° C. will be sufficient for the organocuprate addition reaction to selectively produce the intended product.

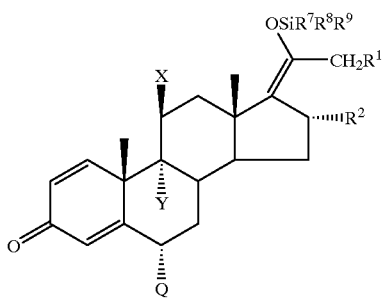

wherein $R^2$ is $C_1$–$C_4$ alkyl, and is most preferably $CH_3$; and X, Y, Q, $R^1$, $R^7$, $R^8$, and $R^9$ are as defined above.

Preferred compounds of Formula II are those where $R^1$ is $CH_3$; $R^2$ is $CH_3$; Q and Y are H; X is $OSiR^7R^8R^9$ and $R^7$, $R^8$, and $R^9$ are $CH_3$ According to the methods of the present invention, enol silyl ethers of Formula II are reacted in a suitable solvent with an alkylating agent, $R^3CH_2Z$, and an enol silyl ether cleaving agent to give the corresponding 16α, 17α-dialkylated steroid of Formula III. Subsequently, the protecting group at the 11-position can be removed ((OSiR$^7$R$^8$R$^9$ or OC(=O)R$^6$)→OH) using known methods (e.g., U.S. Pat. No. 4,012,510 and Cairns, et al., J. Chem. Soc., Perkin Trans. I, 1981:2306), to obtain a medicinally useful 16α, 17α-dialkylated steroid.

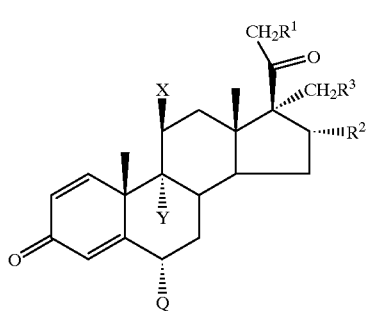

(III)

wherein R$^3$ is H, C$_1$–C$_3$ alkyl, C≡CH, CH=CH$_2$, or phenyl; and

X, Y, Q, R$^1$, and R$^2$ are as defined above.

The general chemical methodology involved is known for other applications. See Kuwajima, et al., J. Am. Chem. Soc., 104:1025 (1982) (fluoride salt method); Patterson, et al., J. Org. Chem., 39:2506 (1974) and Binkley, et al., J. Org. Chem., 40:2156 (1975) (lithium amide method). According to these references, such methods result in little formation of polyalkylated side products.

The alkylating agents, R$^3$CH$_2$Z, suitable for use in the methods of the present invention are known compounds. R$^3$ is selected from the group consisting of hydrogen, an alkyl group of up to three carbon atoms total, an ethenyl group, an ethynyl group, and a phenyl group. Preferably, R$^3$ is H. Z is Cl, Br or I, and is preferably I.

The enol silyl ether cleaving agent is selected from the group consisting of a fluoride salt and lithium amide. A third type of known enol silyl ether cleaving agents, alkyllithium compounds, is not suitable for use in the methods of the present invention because such compounds preferentially react with the 3-keto group rather than the 17(20)-enyl-20-silyl ether.

In the event that a fluoride salt is chosen as the enol silyl ether cleaving agent, the fluoride salt is preferably a tetraalkylammonium fluoride compound. An especially preferred fluoride salt is benzyltrimethylammonium fluoride. Suitable solvents for use with the fluoride salt embodiment of the present invention include tetrahydrofuran ("THF") and glyme. The preferred solvent for use with a fluoride salt is THF. In the case of a fluoride salt enol silyl ether cleaving agent, the alkylation reaction is preferably conducted in the presence of a suitable drying agent, such as zeolite molecular sieves (see Kuwajima, et al., J. Am. Chem. Soc., 104:1025 (1982)).

If lithium amide is chosen as the enol silyl ether cleaving agent, the preferred solvent is liquid ammonia. A cosolvent, such as THF, is optionally employed.

The following examples are presented to illustrate further various aspects of the present invention, but are not intended to limit the scope of the invention in any respect.

EXAMPLE 1

Preparation of 16α,21-Dimethyl-11β,20-bis(trimethylsiloxy)-pregna-1,4, 17(20)-trien-3-one a) Preparation of dilithium dimethyl(cyano)cuprate(I). Methyllithium (1.0 M in 9:1 cumene-THF, 4.0 mL, 4.0 mmol) was added dropwise via syringe over 5 min to a stirred, ice-cooled suspension of CuCN powder (187 mg, 2.09 mmol) in anhydrous THF (6.0 mL) under Ar, giving a clear, pale pink-purple solution of Me$_2$Cu(CN)Li$_2$ (0.2 M).

b) Preparation of Pregna-1,4,16-trien-11β-ol-3,20-dione.

i) The method of Kovendi et al., Rev. Chim. (Bucharest), 27:467 (1976) was modified. Semicarbazide hydrochloride (7.1 mL of a 5% aq. solution, 3.2 mmol) was added to a stirred, 50° C. solution of 21-deoxyprednisolone (1.82 g, 5.29 mmol) [see U.S. Pat. No. 3,033,873 and Vitali et al., Gazz. Chim. Ital., 96:1115 (1966)] in acetic acid (60 mL) under Ar. The solution was heated to 75–80° C. (internal). After 2.7 h, another 4.7 mL of 5% aq. semicarbazide hydrochloride (2.1 mmol) was added. After 5.5 h at 75° C., water (50 mL) was added and the solution was heated to 75° C. for 10 h and then to 90° C. for 1.5 h. The solution was cooled to room temperature, poured into 600 mL of water, stirred for 1 h, diluted with water to 1 L, stirred for 0.5 h and filtered on a fritted Buchner funnel. The solid was dried at 80° C. for 3–4 h to a constant weight of 1.00 g (58%, nominal) of crude product, C$_{21}$H$_{26}$O$_3$.

Proton NMR (CDCl$_3$): d 1.22 (s, 3H, 18-H$_3$); 1.48 (s, 3H, 19-H$_3$), 2.27 (s, 3H, 21-H$_3$); 1.0–2.7 (m, 12H); 4.38 (br q, 1H, J=2.5, H-11); 6.00 (s, 1H, H-4); 6.25 (dd, 1H, J=10 and 2, H-2); 6.66 (q, 1H, J=2, H-16); 7.32 (d, 1H, J=10, H-1). This material was converted in 75% yield to the known trimethylsilyl derivative, 11β-(trimethylsiloxy)-pregna-1,4,16-trien-3,20-dione (Formula I where X=OSi(CH$_3$)$_3$; Y=Q=H), as described in U.S. Pat. No. 4,012,510.

ii) The method of Kovendi et al., Rev. Chim. (Bucharest), 27:467 (1976) was modified. Semicarbazide hydrochloride (4.75 mL of a 5.0% aq. solution, 2.14 mmol) was added to a stirred solution of 21-deoxyprednisolone (2.15 g, 6.25 mmol) [see U.S. Pat. No. 3,033,873 and Vitali et al., Gazz. Chim. Ital., 96:1115 (1966)] in acetic acid (72 mL) under Ar. The solution was heated to 80–85° C. (bath) for 4.2 h. Water (75 mL) was added and heating (85° C. bath) was continued for 5.5 h. The solution was cooled to 23° C. over 11 h, poured into water (850 mL), cooled in ice (to 7° C.) and filtered on a fritted Büchner funnel. The solid was dried under vacuum to give 1.40 g (69%, nominal) of crude product, C$_{21}$H$_{26}$O$_3$.

Proton NMR (CDCl$_3$): d 1.22 (s, 3H, 18-H$_3$); 1.48 (s, 3H, 19-H$_3$), 2.27 (s, 3H, 21-H$_3$); 1.0–2.7 (m, 12H); 4.38 (br q, 1H, J=2.5, H-11); 6.00 (s, 1H, H-4); 6.25 (dd, 1H, J=10 and 2, H-2); 6.66 (q, 1H, J=2, H-16); 7.32 (d, 1H, J=10, H-1). This material was converted in 83% yield to the known trimethylsilyl derivative, 11β-(trimethylsiloxy)-pregna-1,4,16-trien-3,20-dione (Formula I where X=OSi(CH$_3$)$_3$; Y=Q=H), as described in U.S. Pat. No. 4,012,510.

c) Preparation of 21-Methyl-11β-(trimethylsiloxy)-pregna-1,4,16-trien-3,20-dione.

Lithium hexamethyldisilazide (estimated 0.9 M in THF, 2.1 mL, 1.9 mmol) was added over 8 min. to a stirred, cooled (−60 to −65° C. internal) solution of 11β-(trimethylsiloxy)-pregna-1,4,16-trien-3,20-dione (0.73 g, 1.83 mmol) in THF (12.0 mL) and HMPA (3.0 mL) under Ar. After a further 2 min, the cloudy pale-orange mixture was quenched rapidly with iodomethane (2.5 mL, 40 mmol) whereupon the temperature rose to −57° C. and the suspension cleared. The solution was warmed over 2 min to 10° C., quenched with sat. KH$_2$PO$_4$, and partitioned with EtOAc. The organic solution was dried (MgSO$_4$), filtered and concentrated. The residue (1.9 g) was purified by chromatography (80 g silica, 25% to 50% EtOAc-hexanes) to give 0.62 g (82%) of the product, C$_{25}$H$_{36}$O$_3$Si, as an off-white solid, m.p. 178–182° C. (dec.).

Proton NMR (CDCl$_3$): d 0.24 (s, 9H, Me$_3$Si); 1.05 (t, 3H, J=7.3, Me-21); 1.18 (s, 3H, 18-H$_3$); 1.41 (s, 3H, 19-H$_3$); 1.0–2.8 (m, 11H); 2.6 (q, 2H, 21-H$_2$); 4.37 (br q, 1H, J=2.5, H-11); 5.99 (s, 1H, H-4); 6.25 (dd, 1H, J=10 and 2, H-2); 6.64 (q, 1H, J=2, H-16); 7.12 (d, 1H, J=10, H-1).

d) Addition.

To a stirred, cooled (−45° C. bath, MeCN—CO$_2$) solution of 21-methyl-11β-(trimethylsiloxy)-pregna-1,4,16-trien-3,20-dione (0.395 g, 0.96 mmol) in 9.0 mL of anhydrous THF under Ar was added via syringe chlorotrimethylsilane (0.50 mL, 4.0 mmol), followed by dropwise addition over 3 min of 5.0 mL (1.0 mmol) of the above cuprate solution. After 10 min, the mixture was quenched at −45° C. (bath) by rapid addition via syringe of a solution of 0.5 mL (12 mmol) of MeOH and 1.5 mL (11 mmol) of Et$_3$N and warming to 0° C. Water and EtOAc were added and the solution was stirred vigorously. The pH was adjusted from 9 to 7 with sat. KH$_2$PO$_4$ and stirring was continued for 0.5 h. The layers were separated and the organic solution was washed with water and brine, dried (MgSO$_4$), filtered and concentrated. The residue was purified by chromatography to give 0.41 g (85.5%) of the desired product, C$_{29}$H$_{48}$O$_3$Si$_2$, as a white solid.

Proton NMR (CDCl$_3$): d 0.20 (s, 9H, Me$_3$Si); 0.24 (s, 9H, Me$_3$Si); 0.96 (d, 3H, J=6.9, Me-16); 1.01 (t, 3H, J=7.4, Me-21); 1.07 (s, 3H, 18-H$_3$); 1.39 (s, 3H, 19-H$_3$); 0.9–2.4 (m); 2.6 (br m, 3H, 20-H$_2$ and H-16); 4.38 (br s, 1H, H-11); 6.01 (s, 1H, H-4); 6.28 (dd, 1H, J=10and 2); 7.12(d, 1H, J=10).

EXAMPLE 2

Preparation of 11β-(Trimethylsiloxy)-16α, 17α,21-trimethylpregna-1,4-dien-3,20-dione (a). Preparation of reagents. A 3 gram sample of benzyltrimethylammonium fluoride hydrate was dried at 55° C./0.2 Torr (Abderhalden, MeOH) for 40 h, then transferred under Ar to an Ar-filled desiccator over P$_2$O$_5$. Molecular sieves (4A, 1/16 in. spheres) were dried at 250° C. (internal) for several hours and cooled in the desicator. Iodomethane was dried over 4A molecular sieves.

(b). Alkylation. Molecular sieves (2.7 g) and benzyltrimethylammonium fluoride (0.8 g) were weighed under Ar (glove bag) into an oven-dried (100° C.) 25-mL 2-neck round bottom flask containing a magnetic stir bar. THF (3.0 mL, freshly distilled from a potassium-benzophenone solution under Ar) was added via syringe and the mixture was stirred rapidly under Ar for 6 h. To the resulting paste was added via syringe a solution of 16α,21-dimethyl-11β,20-bis (trimethylsiloxy)-pregna-1,4,17(20)-trien-3-one (47 mg, 0.094 mmol) in iodomethane (1.3 mL, 21 mmol). The mixture was stirred for 45 min at rt. Ethyl acetate was added and the suspension was filtered, rinsing well with ethyl acetate. The filtrate was washed with half-saturated brine, dried (MgSO$_4$), filtered through a pad of Florisil with EtOAc and concentrated to give 46.5 mg of an oil that solidified on standing. Crystallization from 12% EtOAc-hexanes (6 mL) at −25° C. followed by drying under vacuum at 75° C. afforded 26 mg (63%) of a white solid, C$_{27}$H$_{42}$O$_3$Si.

Proton NMR (CDCl$_3$): d 0.20 (s, 9H, Me$_3$Si); 0.87 (d, 3H, J=7.2, Me-16); 0.94 (s, 6H, Me-17+18-H$_3$); 1.04 (t, 3H, J=7.1, Me-21); 1.37 (s, 3H, 19-H$_3$); 2.34 (q, 2H, J=7, 21-H$_2$); 1.1–2.7 (m); 3.07 (m, 1H, H-16); 4.46 (br t, 1H, J=3, H-11); 6.00 (s, 1H, H-4); 6.27 (dd, 1H, J=10 and 2, H-2); 7.10 (d, 1H, J=10, H-1).

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of preparing a 16α, 17α-dialkylated steroid of the formula

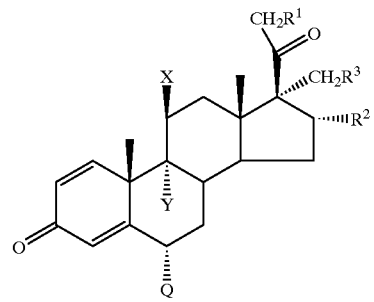

wherein R$^1$ is H or CHR$^4$R$^5$;

R$^2$ is C$_1$–C$_4$ alkyl;

R$^3$ is H, C$_1$–C$_3$ alkyl, C≡CH, CH=CH$_2$, or phenyl;

X is OSiR$^7$R$^8$R$^9$ or OC(=O)R$^6$;

Y is H, F, or Cl; or X and Y taken together are a covalent bonds; or X and Y taken together form an epoxide group;

R$^4$, R$^5$ and R$^6$ are independently H or C$_1$–C$_4$ alkyl;

R$^7$, R$^8$ and R$^9$ are independently C$_1$–C$_4$ alkyl; and

Q is H or CH$_3$;

comprising reacting in a solvent an enol silyl ether of the formula

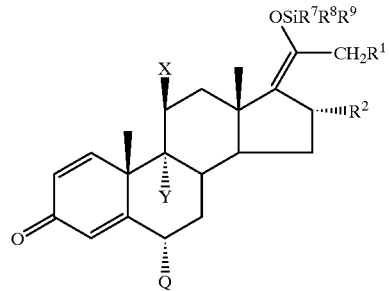

with an enol silyl ether cleaving agent and an alkylating agent of the formula R$^3$CH$_2$Z wherein R$^3$ is selected from the group consisting of hydrogen, a primary alkyl group of up to three carbon atoms total, an ethenyl group, an ethynyl group, and a phenyl group; and Z is Cl, Br or I.

2. The method of claim 1 wherein $R^1$ is $CH_3$; $R^2$ is $CH_3$; Q and Y are H; X is $OSiR^7R^8R^9$ and $R^7$, $R^8$, and $R^9$ are $CH_3$.

3. The method of claim 1 wherein $R^3$ is H and Z is I.

4. The method of claim 1 wherein the enol silyl ether cleaving agent is selected from the group consisting of a fluoride salt and lithium amide.

5. The method of claim 4 wherein the enol silyl ether cleaving agent is a tetraalkylammonium fluoride salt.

6. The method of claim 5 wherein the enol silyl ether cleaving agent is benzyltrimethylammonium fluoride.

7. The method of claim 5 wherein the solvent is selected from the group consisting of tetrahydrofuran and glyme.

8. The method of claim 7 wherein the solvent is tetrahydrofuran.

9. The method of claim 4 wherein the enol silyl ether cleaving agent is lithium amide and the solvent is liquid ammonia.

* * * * *